(12) United States Patent
Sacco et al.

(10) Patent No.: US 8,114,063 B2
(45) Date of Patent: Feb. 14, 2012

(54) RFID-TAGGED URINARY CATHETER

(76) Inventors: John J. Sacco, Fayetteville, NY (US);
Brett B. Greenky, Manlius, NY (US)

( * ) Notice: Subject to any disclaimer, the term of this patent is extended or adjusted under 35 U.S.C. 154(b) by 483 days.

(21) Appl. No.: 12/116,579

(22) Filed: May 7, 2008

(65) Prior Publication Data

US 2009/0281523 A1    Nov. 12, 2009

(51) Int. Cl.
*A61M 25/00* (2006.01)

(52) U.S. Cl. ...................................... 604/523

(58) Field of Classification Search ............. 604/523, 604/19, 317, 327, 48, 93.01, 264, 500, 540, 604/544; 340/572.8, 572.1; 705/2–3; 235/492, 235/380, 385; 600/300, 407, 437; 700/214–215; 606/1, 34

See application file for complete search history.

(56) References Cited

U.S. PATENT DOCUMENTS

| | | |
|---|---|---|
| 4,858,615 A | 8/1989 | Meinema |
| 5,425,375 A | 6/1995 | Chin et al. |
| 5,425,713 A | 6/1995 | Taylor et al. |
| 5,720,293 A | 2/1998 | Quinn et al. |
| 5,916,153 A | 6/1999 | Rhea, Jr. |
| 6,264,613 B1 | 7/2001 | Pfeiffer et al. |
| 6,308,089 B1 | 10/2001 | von der Ruhe et al. |
| 6,651,669 B1 | 11/2003 | Burnside |
| 2004/0236606 A1 | 11/2004 | Oishi et al. |
| 2006/0065713 A1* | 3/2006 | Kingery ..................... 235/380 |
| 2007/0083111 A1* | 4/2007 | Hossack et al. .............. 600/437 |
| 2007/0083286 A1 | 4/2007 | Kobayashi |
| 2007/0139202 A1 | 6/2007 | Austin |
| 2009/0048870 A1* | 2/2009 | Godshall et al. ................ 705/3 |
| 2009/0315864 A1* | 12/2009 | Silverbrook et al. ......... 345/179 |

* cited by examiner

*Primary Examiner* — Tatyana Zalukaeva
*Assistant Examiner* — Benedict L Hanrahan
(74) *Attorney, Agent, or Firm* — Bernhard P. Molldrem, Jr.

(57) ABSTRACT

A hand-held RFID scanner appliance is employed to capture and display status of urinary catheters in hospital patients. The patients are provided with RFID wrist bracelets, and catheters are provided with RFID tags, each with a unique identification code. When the nurse performs a catheter insertion, the nurse scans the patient wrist bracelet with the appliance, then scans a selected catheter. After the catheter is successfully inserted, the catheter is scanned a second time. This creates a time stamp, and a data entry is recorded with the patient identity, presence of catheter, and time of insertion. The appliance is synchronized to the hospital server, and the catheterization status of the hospital patients is displayed for the medical practitioners. This process aids in preventing hospital-acquired urinary tract infections.

9 Claims, 1 Drawing Sheet

RFID-TAGGED URINARY CATHETER

BACKGROUND OF THE INVENTION

This invention relates to a technique of accounting for the presence of a urinary catheter or other indwelling catheter in a hospital patient, and is more specifically concerned with a technique that permits scanning of the patient with a scanning device for that purpose. The invention is more specifically concerned with a technique for indicating the presence or absence of a catheter in a hospital patient, and maintaining a log of patients with catheters and of the time and date when the catheter is to be removed.

The invention is more particularly concerned with a technique that employs uniquely coded radio frequency identity (RFID) chips or tags and one or more RFID scanners adapted to track the use of the catheters.

Hospital-acquired infections of patients are, at the current time, a major problem in medicine, both as a significant drawback to patient care, and also as a significant cost to hospitals, one which is not reimbursable. Urinary tract infections, or UTI, are the most common hospital-acquired infection, and UTIs have been linked to the use of urinary catheters. At present, one in four hospitalized patients is fitted with a urinary catheter. Each year, urinary catheters trigger a half million or more cases of urinary tract infection. However, many patients do not require catheters, and many others do not need them beyond a day or two of their hospitalization. Urinary catheters are often ordered only as a precaution after some types of surgeries. Hospitals do not have any reliable system to keep track catheter use, and many hospitals do not keep track of which patients have catheters. It is estimated that only about one in ten hospitals conducts a daily check of the patient to see if catheter use is still needed. As a result a large share of hospital patients have catheters for several days longer than is necessary, and this extended use of urinary catheters leads to UTIs. About one percent of the patients administered a urinary catheter will get a urinary tract infection. All of those patients will require antibiotics, and some of them at least will suffer life-threatening complications.

The added cost of treating a patient for a hospital-acquired urinary tract infection is significant. Each episode of symptomatic nosocomial UTI costs at least $600, and each episode of UTI-related bloodstream infection results in even higher costs, conservatively at least $2,800. The problem is compounded in that many infections are asymptomatic, and patients can be administered an antibiotic simply for the reason that they have an indwelling catheter. The administration of an antibiotic can be inappropriate, as it can enable the infectious organisms to become multi-drug resistant, and very difficult to treat later on.

Moreover, many third-party payors, e.g., health insurance plans, do not or will no longer reimburse hospitals for hospital-acquired preventable complications. Medicare will no longer pay for various preventable hospital errors, including not only surgical errors and injuries from falls, but also catheter-related urinary tract infections. The hospital cannot bill the injured patients for the added costs of treatment. The only recourse is for the medical practitioners to ensure the catheter is not left in when it is not needed.

Catheters are widely used even though need for urinary catheters is often unjustified and is unnecessary for most patients for about one-third of the days that the patients are catheterized. Moreover, the treating physician can often be completely unaware that a catheter is in place. A majority of hospitals do not monitor for catheter duration. As a result, the physicians are not writing orders to have the catheters removed, even when they are unnecessary or no longer necessary. It has thus become incumbent on the patient, or the patient's family, to ask the doctor or nurse, every day, whether the catheter is still really necessary or if it can be removed, but the patient or his or her family does not know they should do this, and it should not be the patient's burden to have to remind the doctor or nurse about the catheter.

In the past, some steps have been taken to reduce the incidence of catheter-related UTI. These include the use of catheters that are coated with an anti-bacterial agent to inhibit bacterial growth, or the use of an anti-microbial agent in the urine collection bag. However, these have not proven to be effective in reducing UTI. Other techniques involve using condom-style catheters, which at least reduce the risk of bacteria entering the urethra, or supra-pubic catheters, but the latter involves actually having to penetrate the abdomen and bladder of the patient, and can result in complications. Portable ultrasound bladder scanners can be used to see if the patient's bladder is being emptied without a catheter, but most hospitals do not use that system on any regular basis.

Accordingly, some simple technique is needed to identify those patients that have a urinary catheter, to track the time of use of the catheter, and to ensure that the catheter is not left in place any longer than necessary. By removing the catheter as soon as it is no longer needed, the major cause of hospital-caused UTI will be avoided, and the cost and medical risk involved in hospitalization will be reduced significantly. This technique can also be used for any other indwelling catheter.

OBJECTS AND SUMMARY OF THE INVENTION

It is therefore an object of the present invention to improve the techniques used in tracking catheter use, in identifying which patients have a catheter, and in tracking the duration of catheter use for those patients.

A related object of this invention is to remove or avoid a major cause of hospital-acquired urinary tract infections.

A further object of the present invention is to provide a technique that is simple for the nurse or other practitioner to employ when catheterizing a patient and when later visiting the patient, and which provide the nurse or other practitioner the information necessary to decide when to remove the catheter from the patient.

Another object of the present invention is to provide a means of tracking catheter use which is compatible with the hospital computer network.

According to an aspect of this invention, there is a supply of urinary catheters for the hospital patients for whom a catheter has been prescribed. Each catheter typically includes a flexible tube adapted to be inserted into the urethra, i.e., urine duct, of the patient and to remain in place until removed. An external portion of the catheter has a fitting adapted to be attached to a drainage bag or other urine collection receptacle. Catheter RFID tags, each having a unique scannable ID code, are attached onto or incorporated onto the external part of the catheter for uniquely identifying each urinary catheter. The patients are provided with patient identity wrist bracelets, each incorporating a respective patient RFID tag. The bracelet RFID tags each have a unique scannable ID code uniquely identifying the associated patient.

The nurse is provided with a hand-held scanner device that is adapted for scanning the catheter RFID tags and the patient RFID tags. The device has a display visible to the nurse, a suitably programmed internal processor, and software which begins an insertion sequence upon the scanning of one of said patient RFID tags. After the patient bracelet RFID tag is scanned in, the nurse scans the RFID tag of one of said catheters, and then re-scans the catheter RFID tag. This produces a time stamp of a successful catheter insertion upon the second scanning of the catheter RFID tag. A log entry is created in the device indicating successful catheter insertion and time of insertion, as well as identity of the patient. This information is stored and displayed. The information is visible to the practitioner including the patient identity, presence or absence of one of the catheters in the said patient, and time of insertion of the catheter in the patient. The duration of the catheter is then tracked, either in terms of the length of time that the catheter has been in place, or in terms of the time remaining until the catheter is scheduled to be removed.

Where the urinary catheter is a Foley catheter, i.e., the type having an inflation port, the associated RFID tag can be affixed onto the inflation port.

An application server for this system is capable of communicating with the hand-held device(s) for storing patient data and catheter data based on information scanned into said hand held device. The application server has embedded software for producing report(s) listing the identity of each patient who has been administered a catheter, and listing an associated targeted removal time for each such patient.

The hand held scanning device can display a listing of all the patients (for a given floor or for a given nursing station responsibility) as well as a listing of the targeted removal times. The device can also have an operator-actuated status switch to enter a removal of a catheter from the associated patient. The hand held device favorably has a capability for displaying the individual patient identity and target time for removal of catheter upon scanning of the wrist bracelet of the that individual patient.

The hand-held device synchronizes with a central server by communicating with the server, either wirelessly or by means of a docking station. This provides current catheterization status to the central computer network, and that can be uploaded onto other similar hand-held scanner devices.

This technique makes it possible for nurses and treating physicians to recognize which patients have a catheter in place, and the duration of the catheterization, so that the doctor can make an informed decision to remove or retain the catheter for each patient. The catheter removal orders can be uploaded to the hand held devices, and displayed for each patient.

The catheter RFID can also be scanned by the hand held device or by any other suitable RFID device for the purpose of alerting practitioners to the fact that the catheter is in place.

For a better understanding of these and other objects and advantages of the present invention, reference will be made to the following detailed description of a preferred embodiment of the invention which is to be read in conjunction with the accompanying Drawing Figures.

DETAILED DESCRIPTION OF A PREFERRED EMBODIMENT

Figures 1, 2:
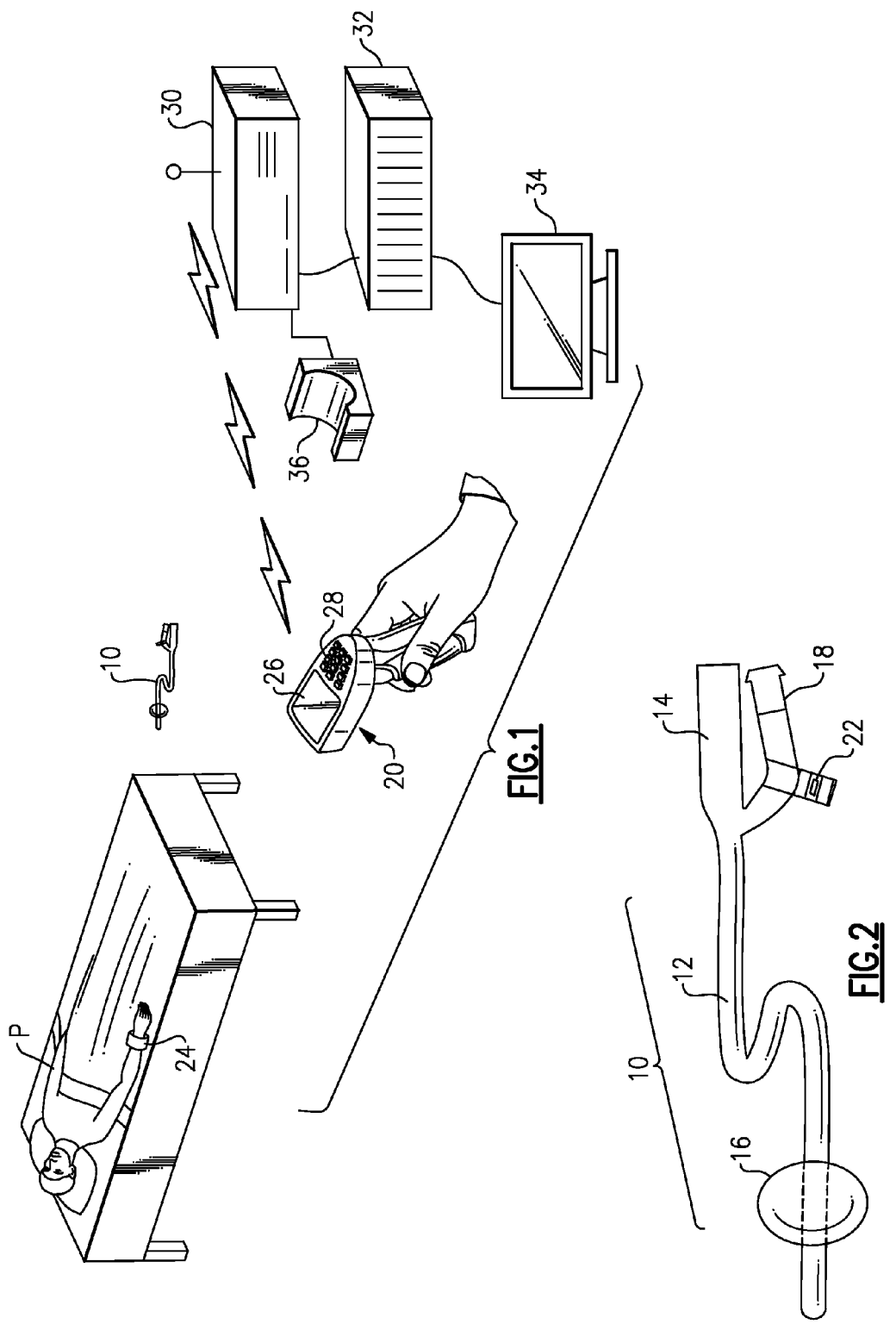
FIG. 1 is a general schematic view illustrating the equipment and usage of the RFID-based urinary catheter monitoring system according to one embodiment of the invention.
FIG. 2 shows a typical Foley type catheter, provided with an RFID tag, as employed in this embodiment.

Referring now to the Drawing, FIG. 1 illustrates the general arrangement of the equipment employed in this invention. A hospital patient P may be provided with a catheter 10, shown in more detail in FIG. 2, which is inserted into the patient P to assist in the drainage and collection of urine. The catheter remains in place for some period of time, and is considered an indwelling catheter. Also shown in FIG. 1 is a hand-held scanning appliance 20 capable of scanning and reading radio-frequency codes from RFID devices, as well as an application server 30. Here the RFID scanning appliance 20 and the server 30 are shown as communicating via a radio link, but the two devices may communicate via other means, such as a docking station 36 for the appliance 20.

As shown in FIG. 2 the catheter 10 is formed of an elongated flexible hollow tube 12 that is to be inserted via the patient's urethra into the bladder. There is drainage port 14 at the external terminus, and this is designed to connect to a urine drainage bag or other collection means (not shown). There is a balloon 16 positioned at the distal end of the tube 12 near the tip. After insertion, the balloon 16 is inflated with distilled water, which is injected through an inflation port 18 at the external end of the catheter 10. The inflated balloon 16 keeps the tube 12 from being ejected from the patient's bladder, but can be easily deflated for decatheterization by draining the water out the inflation port 18.

In this case, the catheter 10 has an RFID tag 22 attached onto the external end, e.g., on the inflation port 18. This RFID tag 22 contains a unique code that can be transmitted to the scanner appliance 20 when the tag 22 is interrogated, and that code identifies the specific catheter 10. Each other catheter will have a similar tag 22, each with an individual unique code.

Returning to FIG. 1, The patient P is provided with patient identification bracelet or wrist-band 24, and each wrist-band has an embedded RFID tag containing a unique RFID code that uniquely identifies the patient.

As also shown in FIG. 1, the hand held scanner appliance 20 has a screen or display 26 for displaying patient and catheter information, and also has a keypad 28 for entering data or for commencing an operation, i.e., catheter insertion or removal. Instead of a keypad, the appliance could use a touch screen to serve the purposes of both display screen and keypad.

The application server 30 is connected to a hospital computer network 32, and that network may be accessed at various stations, represented here by a computer monitor screen 34.

Each patient P is uniquely assigned an RFID bracelet 24. This bracelet is associated with data in the application server 30, to include patient identity and location (name, room assignment, etc.), name of treating physician, as well as other relevant treatment information for that patient. The application server 30 maintains data about all patients who currently host a catheter, as well as the time of catheterization. The application server also tracks catheterization orders and removal orders. Target removal time(s) are configurable at the application server.

The software application running on the server 30 will provide an interface for pending catheterization requests to be entered. The server software application displays a list of the catheterizations that are pending, and whether of not these are initial catheterizations, removals, or replacements. The application provides the nurse(s) with a list of catheterization procedures to be performed, and how many catheters and bracelets will be needed to complete them.

The nurse, or other practitioner who is to perform the catheterization procedure, first retrieves an RFID catheter 10, and a portable scanner appliance 20. If this is an initial catheterization for the patient P, the patient's RFID bracelet 24 is also obtained and placed on his/her wrist. The patient identity is entered into the system by the scan of the bracelet 24.

In the patient room, the bracelet 24 is scanned. The patient's name and other identifying data as indicated by the RFID scanner appliance on the display 26 are compared with the patient's chart. If this is the patient's first catheter, the bracelet is applied to the patient at this time, and scanned in, i.e., applied both physically and logically. The catheter 10 is then scanned prior to insertion. The RFID scanner appliance 20 then associates the scanned catheter 10 with the patient P. The catheter is inserted in the patient. If the insertion is successful, the catheter 10 is re-scanned, and at that time the RFID scanner appliance 20 considers the procedure complete, and a timestamp is recorded. If there is some problem with this catheter, and it cannot be inserted, the nurse may scan a second catheter 10, which has its own RFID tag 22. This logically terminates the insertion of the first catheter and commences the insertion of the second one. Then, scanning the second catheter 10 after insertion indicates a successful insertion procedure, and creates the timestamp, as discussed before. Scanning the same catheter both prior to insertion and post-insertion indicates a successful procedure. Visual feedback, presented on the video display 26 of the scanner appliance 20, guides the nurse through this procedure.

The nurse can then perform the catheter procedures that have been ordered for a number of patients, using the same scanner appliance. Appliance 20 can transmit catheter transaction data back to the application server by the radio link, as illustrated. Alternatively, the appliance 20 can be returned to the docking station 36, which transfers data between the appliance and the server. Catheter transaction data are uploaded to the server at that time, and any updated data will be downloaded to the RFID scanner appliance 20, as appropriate.

Both the application that is running on the application server 30 and the embedded application software on the RFID scanner appliance 20 are capable of generating alert messages. These alert messages may be visual or audible, may involve email or may leverage an external paging system. The alert messages remind the users, i.e., the medical practitioners, of specific patients for whom a catheter is due for replacement or removal, as well as those who are already overdue for replacement/removal.

The application server is capable of generating reports indicating which catheters are in need of replacement and/or removal within a given time span, i.e., during a nursing shift. These reports may be arranged in sequential time order, i.e. by target removal time, or may be listed in terms of room or floor sequence. The nurse may select the order that is best suited to use as a job checklist. The reports may be made available to the RFID scanner appliance 20, and may also be made available to computer monitor screen 34 at the nursing station. The data presented will be as current as the most recent synchronization of the RFID scanner appliance 20.

The display 26 of the appliance 20, while idle, shows a list of all the patients with catheter expiry times, as well as time remaining for each. When a given patient's wrist-band or bracelet 24 is scanned, then the appliance display 26 will show only the identity, expiration time, and time remaining for that patient P. Scanning a bracelet 24 followed by scanning of the RFID tag 22 of a catheter 10 will commence a catheter insertion workflow. The insertion workflow may be aborted by depressing one of the keys of the keypad 28. Scanning a catheter RFID tag 22 will present an interface with which the nurse can follow procedures on the screen 26 so as to indicate that the catheter has been successfully removed.

While an RFID tag or chip 22 is shown on a Foley urinary catheter in this embodiment, it should be understood that this technique can be employed for tracking the use of any sort of indwelling catheter. This system may be employed for veterinary as well as human medical purposes. There are other technologies that could be employed for embedding a unique identifying code on the catheter and on the patient bracelet. Rather than discrete tags 22, microscopic RFID chips, (RFID powder) may be incorporated into the material of the catheter device. In some cases, the bracelet may not be placed on the wrist, but may be more appropriately placed elsewhere on the patient.

As mentioned before, once the urinary catheter is inserted, the RFID can be scanned by other devices to indicate to a treating physician or a nurse that there is a catheter present in the patient.

Because the system keeps accurate track of the insertion times and presence of these catheters in patients, and because the nurses and doctors are presented with an accurate and updated list of catheterizations, the physicians can make informed treatment decisions, so that the catheters can be removed as soon as they are no longer required. This will cut down significantly on the incidents of hospital-acquired UTI, and will result in reduced costs and enhanced patient treatment success.

While this invention has been explained with reference to the particular structure disclosed herein, it is not confined to the details as set forth and this application is intended to cover any modifications and changes as may come within the scope of the following claims.

We claim:

1. Method of tracking indwelling catheter use in hospital patients, in which designated health care practitioners are responsible for inserting catheters in said hospital patients, and in which a plurality of machine-readable tags are placed upon respective ones of said hospital patients, and on a plurality of catheters, each said tag having a unique identification code, and wherein a computerized hospital information system contains patient demographic information including identity of each patient and room location of each patient, the method comprising:

scanning the patient tag for one of said patients on a portable scanner appliance;
   selecting one of said catheters for insertion in the patient;
   scanning the tag of the selected one of the catheters with said scanner appliance to commence a catheterization sequence in which the scanner appliance electronically associates the selected one of the catheters with said patient; and
   after scanning the tag thereof, the designated health care practitioner inserting said catheter in the patient;
   the scanner appliance uploading to said hospital information system the catheterization data to include identity location of each such patient, and date/time stamp of the insertion of each said catheter in said patients;
   the method then comprising the step of computing for said patient, in the hospital information system, a catheter target removal time;
   storing catheterization data for each said patient including at least the presence of the catheter in said patient, the date stamp of the time of insertion thereof; and said hospital information system being suitably programmed for automatically computing the catheter target removal time for each said patient and generating alerts when a target removal time has been reached for any said patient; and presenting said alerts to the designated healthcare practitioner identifying each patient for whom the associated target removal time has been reached; and comprising uploading current catheterization status from said hand held scanner appliance to a central hospital network associated with said hospital information system, and downloading catheterization status, including said alerts, for said hospital patients from said central hospital network to one or more computer screens available to said designated healthcare practitioners.

2. The method of claim 1, further comprising creating a display on said scanner appliance showing a list of patients having catheters and associated catheterization data for said patients, the catheterization data including for each said patient: patient identity, presence or absence of one of said catheters in said patient, time of insertion of the catheter in the patient, and length of time that the catheter has been in place in the patient.

3. The method of claim 1, further comprising synchronizing catheterization data stored on said scanner appliance with a hospital server.

4. The method of claim 3, wherein said step of synchronizing includes placing said appliance into a docking station that communicates with said hospital server.

5. The method of claim 1 wherein said catheter, after insertion, remains in place in said patient for a period of time.

6. The method of claim 1 wherein said catheter is a urinary catheter and is inserted through said patient's urethra into the patient's bladder.

7. The method of claim 1 wherein, for each patient to whom an indwelling catheter has been administered, said hand held appliance producing a report listing the identity of each such patient who has been administered a catheter, and listing the associated targeted catheter removal time for each such patient.

8. The method of claim 1 further comprising after the step of inserting the catheter in the patient; again scanning the tag of said catheter.

9. The method of claim 8, further comprising, after the step of scanning the tag of a selected one of the catheters,
   selecting a second one of the catheters;
   scanning the tag of the second one of the catheters, the scanning thereof by said scanning appliance being operative to cancel the identity of the first-mentioned catheter in said applicance and to commence an insertion procedure for said second catheter; and then
   continuing, with the second catheter, said steps of inserting the catheter in the patient and again scanning the tag of the catheter.

* * * * *